United States Patent [19]
Koprowski et al.

[11] Patent Number: 5,872,124
[45] Date of Patent: Feb. 16, 1999

[54] TREATMENT OF DISEASES OF THE CENTRAL NERVOUS SYSTEM USING URIC ACID AS A SCAVENGER OF PEROXYNITRITE

[75] Inventors: Hilary Koprowski, Wynnewood, Pa.; Douglas Craig Hooper, Medford, N.J.; John L. Farber, St. Davids, Pa.

[73] Assignee: Thomas Jefferson University, Philadelphia, Pa.

[21] Appl. No.: 690,110

[22] Filed: Jul. 31, 1996

[51] Int. Cl.$^6$ ................................................ A01N 43/90
[52] U.S. Cl. .................... 514/261; 514/183; 514/256; 514/262; 514/263
[58] Field of Search ............................... 514/12, 183, 179, 514/740, 261

[56] References Cited

U.S. PATENT DOCUMENTS

| | | | |
|---|---|---|---|
| 5,449,688 | 9/1995 | Wahl et al. | 514/546 |
| 5,455,279 | 10/1995 | Lipton . | |
| 5,464,857 | 11/1995 | Maeda et al. | 514/398 |

FOREIGN PATENT DOCUMENTS

| | | |
|---|---|---|
| 9511231 | 4/1995 | WIPO . |
| 9614842 | 5/1996 | WIPO . |

OTHER PUBLICATIONS

Cross AH, et al, (1994) Aminoguanidine, an inhibitor of inducible nitric oxide synthase, ameliorates experimental autoimmune encephalomyelitis in SJL mice. J Clin Invest 93:2684–2690.

Dawson VL, et al, (1996) Nitric oxide neurotoxicity. J Chem.Neuroanat. 10:179–190.

Heales SJ, et al, (1994) Trolox protects mitochondrial complex IV from nitric oxide– mediated damage in astrocytes. Brain Res. 668:243–245.

Iadecola C, et al, (1995) Inhibition of inducible nitric oxide synthase ameliorates cerebral ischemic damage. Am.J Physiol. 268:R286–R292.

Kooy NW, et al, (1994) Agonist–induced peroxynitrite production from endothelial cells. Arch.Biochem.Biophys. 310:352–359.

Maeda H, et al, (1994) Multiple functions of nitric oxide in pathophysiology and microbiology: analysis by a new nitric oxide scavenger. J Leukoc.Biol. 56:588–592.

Takaaki Akaike et al., Effect of neurotropic virus infection on neuronal and inducible nitric oxide synthase activity in rat brain, Journal of NeuroVirology (1995), vol. 32, 118–125.

Omar Bagasra et al., Activation of the inducible from of nitric oxide synthase in the brains of patients with multiple sclerosis, Proc. Natl. Acad. Sci. USA (Dec. 1995) 12041–12045.

D. Craig Hooper et al., Local nitric oxide production in viral and autoimmune diseases of the central nervous system, Proc. Natl. Acad. Sci. USA (Jun. 1995) 5312–5316.

Hilary Koprowski et al., In vivo expression of inducible nitric oxide synthase in experimentally induced neurologic diseases, Proc. Natl. Acad. Sci. USA (1993) 3024–3027.

Sergei V. Spitsin et al., Characterization and Functional Analysis of the Human Inducible Nitric Oxide Synthase Gene Promoter, Molecular Medicine (Mar. 1996) 226–235.

Takaaki Akaike et al., Antagonistic Action of Imidazolineoxly N–Oxides against Endothelium–Derived Relaxing Factor/˙NO through a Radical Reaction, Biochemistry (1993), vol. 32, 827–832.

Nuran Akgören et al., Importance of nitric oxide for local increases of blood flow in rat cerebellar cortex during electrical stimulation, Proc. Natl. Acad. Sci. USA (1994), vol. 91, 5903–5907.

(List continued on next page.)

*Primary Examiner*—Lora M. Green
*Attorney, Agent, or Firm*—Volpe and Koenig, P.C.

[57] ABSTRACT

The process of treating a disease of the central nervous system with an agent from one or more of the following three classes of agents: (1) nitric oxide scavengers, (2) peroxynitrite scavengers, and (3) agents that either interfere with the synthesis of iNOS in the cell or the enzymatic activity of iNOS in the cell.

5 Claims, 14 Drawing Sheets

OTHER PUBLICATIONS

Joseph S. Beckman, Peroxynitrite versus Hydroxyl Radical: The Role of Nitric Oxide in Superoxide–Dependent Cerebral Injury, Annals New York Academy of Sciences (1994) 69–75.

Avraham Ben–Nun et al., The rapid isolation of clonable antigen–specific T Iymphocyte lines capable of mediating autoimmune encephalomyellitis, Eur. J. Imunol (1981), vol. 11, 195–199.

Anne H. Cross et al., Aminoguanidine, an Inhibitor of Inducible Nitric Oxide Synthase, Ameliorates Experimental Autoimmune Encephalomyelitis in SJL Mice, The American Society for Clinical Investigation, Inc. (1994), vol. 11, 2684–2690.

Laura C. Green et al., Analysis of Nitrate, Nitrite, and [$^{15}$N]Nitrate in Biological Fluids, Analytical Biochemistry 126 (1982), vol. 126, 131–138.

Robert L. Knobler et al., Genetic Regulation of Susceptibility and Severity of Demyelination, Annals New York Academy of Sciences, vol. 540, 735–737.

Robert Korngold et al., Acute Experimental Allergic Encephalomyelitis in Radiation Bone Marrow Chimeras Between High and Low Susceptible Strains of Mice, Immunogenetics (1986), vol. 24, 309–315.

Robin F. Lin et al., Nitric Oxide Localized to Spinal Cords of Mice with Experimental Allergic Encephalomyelitis: An Electron Paramagnetic Resonance Study, J. Exp. Med. (1993), vol. 178, 643–648.

Harald H. H. W. Schmidt et al., NO at Work, Cell (1994), vol. 78, 919–925.

Solomon H. Snyder et al., Biological Roles of Nitric Oxide, Scientific American (May 1992) 68–77.

Klaus Tschaikowsky et al., Induction of nitric oxide synthase activity in phagocytic cells inhibited by tricyclodecan–9–yl–xanthogenate (D609), Br. J. Pharmacol (1994), vol. 113, 664–668.

J. Zielasek et al., Administration of nitric oxide synthase inhibitors in experimental autoimmune neuritis and experimental autoimmune encephalomyelitis, Journal of Neuroimmunology (1995), vol. 58, 81–88.

Hooper et al., Prevention of experimental allergic encephalomyelitis by targeting nitric oxide and peroxynitrite: Implications for the treatment of multiple sclerosis, National Academy of Sciences of the USA (Mar., 1997), vol. 94, pp. 2528–2533.

Akaike et al., Antagonistic Action of Imidazolineoxyl N–Oxides against Endothelium–Derived Relaxing Factor/•NO through a Radical Reaction, Biochemistry (1993), vol. 32, pp. 827–832.

Liu et al., Nitrite and Nitrosamine Synthesis by Hepatocytes Isolated from Normal Woodchucks (*Marmota monax*) and Woodchucks Chronically Infected with Woodchuck Hepatitis Virus, Cancer Research (Aug. 1992), vol. 52, pp. 4139–4143.

Mollace et al., HIV Coating gp 120 Glycoprotein–Dependent Prostaglandin $E_2$ Releases by Human Cultured Atrocytoma Cells ia Regulated Nitric Oxide Formation, Biochemical and Biophysical Research (1994), vol. 203, pp. 87–93.

V. Mollace et al., HIV gp 120 Glycoprotein Stimulates the Inducible Isoform of NO Synthase in Human Cultured Astrocytoma Cells, Biochemical and Biophysical Research (Jul. 1993), vol. 194, pp. 439–445.

J. A. Lyon et al., Inhibition of Nitric Oxide Induction from Avian Macrophage Cell Lines by Influenza Virus, Avian Diseases (1993), vol. 37, pp. 868–873.

V. Dawson et al., Human immunodeficiency virus type 1 coat neurotoxicity mediated by nitric oxide in primary cortical cultures, National Academy of Science of the USA, (1993), vol. 90, pp. 3256–3259.

G Karupiah et al., Inhibition of Viral Replication by Interferon–y–Induces Nitric Oxide Synthase, Reports (1993), vol. 261, pp. 1445–1448.

Melkova et al., Interferon–y– Severely Inhibits DNA Synthesis of Vaccinia Virus in a Macrophage Cell Line, Virology (1994), vol. 198, pp. 731–735.

Y. Zheng et al., Severity of Neurological Signs and Degree of Inflammatory Lesions in the Brains of Rats with Borna Disease Correlate with the Induction of Nitric Oxide Synthase, Journal of Virology, (1993), pp. 5786–5791.

D. Pietraforte et al., gp120 HIV envelope glycoprotein increases the production of nitric oxide in human monocyte–derived macrophages, Journal of Leukocyte Biology, (1994), vol. 55, pp. 175–182.

K. D. Croen, Evidence for an Antiviral Effect of Nitric Oxide, The American Society for Clinical Investigation, (1993), vol. 91, pp. 2246–2452.

E. Butz et al., Macrophages in mice acutely infected with lymphocytic choriomeningitis virus are primed for nitric oxide synthesis, Microbial Pathogenesis (1994), vol. 16, pp. 283–295.

TREATMENT OF DISEASES OF THE CENTRAL NERVOUS SYSTEM USING URIC ACID AS A SCAVENGER OF PEROXYNITRITE

FIELD OF THE INVENTION

The field of the invention is the treatment of diseases of the central nervous system using either a nitric oxide scavenger, a peroxynitrite scavenger, or an agent that interferes with the activity or cellular production of the enzyme, inducible nitric oxide synthase (iNOS).

BACKGROUND

The overproduction in the body of nitric oxide (NO) and/or peroxynitrite (ONOO$^-$) has been suggested by some to be a contributing factor to diseases of the central nervous system, particular those that are immune-mediated and/or inflammatory.

The enzyme iNOS is responsible for the production of nitric oxide during an immune response. Nitric oxide combines with superoxide ($O_2^-$) to form peroxynitrite. Those molecular level considerations are relevant to the present inventions.

An extensively used model system to study multiple sclerosis, an example of a disease treated by the present invention, is experimental allergic encephalomyelitis (EAE) in rats and mice. This model was used for the experiments described below.

BRIEF SUMMARY OF THE INVENTION

The present invention, in a general aspect, is the process of treating a disease diagnosed as a disease of the central nervous system with an agent from one or more of the following three classes of agents: (1) nitric oxide scavengers, (2) peroxynitrite scavengers, and (3) agents that either interfere with the synthesis of iNOS in the cell or the enzymatic activity of iNOS in the cell.

DETAILED DESCRIPTION

Glossary and Definitions

Figure 1:
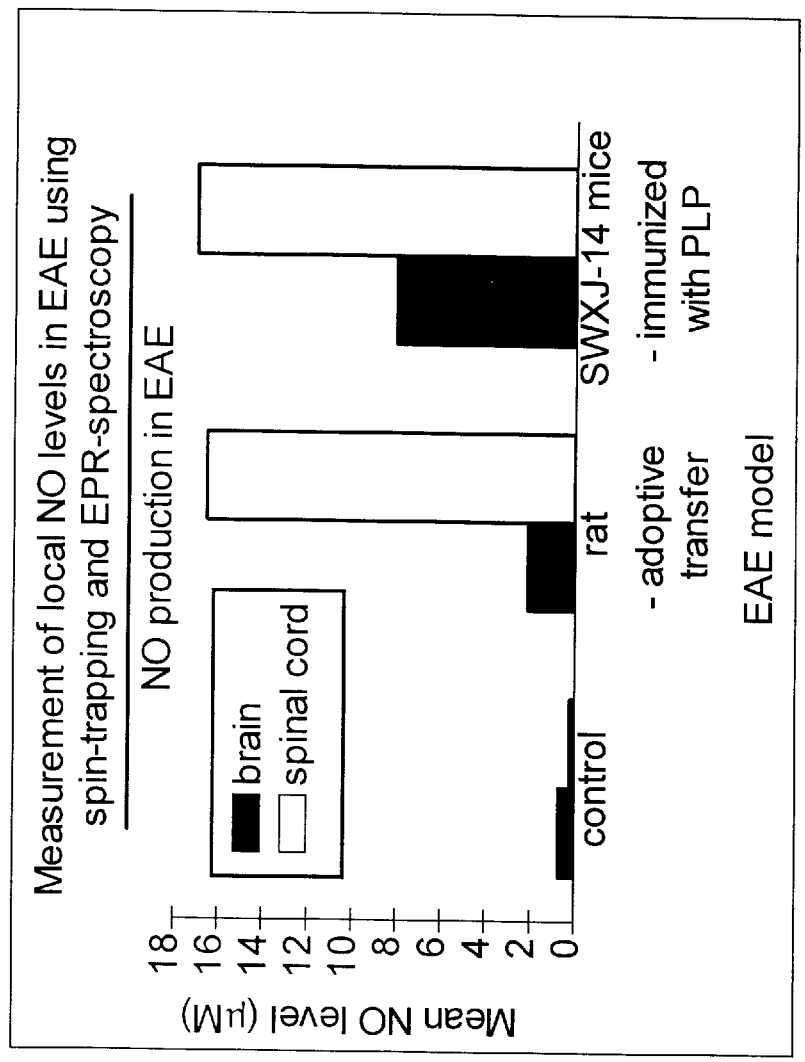
FIG. 1. Measurement of local NO levels in EAE using spin-trapping and EPR-spectroscopy.

"PLP" is proteolytic protein from the myelin sheath, specifically PLP 139-151 (8) (The "8" in parenthesis refers to reference 8, below.)

"MEP" is myelin basic protein, an autoantigen from the myelin sheath of nerves, a target of much damage in multiple sclerosis.

"pMBP" is a peptide with an amino sequence found in MBP.

"MS" is multiple sclerosis.

"PTIO" is 2-phenyl-4,4,5,5-tetramethylimidazoline-1-oxyl-3-oxide.

"Carboxy-PTIO" is 2-(4-carboxyphenyl)-4,4,5,5-tetramethylimidazoline-1-oxyl-3-oxide.

"Uric acid" is 2,6,8-trihydroxypurine.

"D609" is tricyclodecan-9-yl-xanthogenate. D609 is believed to block the activation of PC-PLC by blocking PC-PLC activation.

"AIDS" is acquired immune deficiency syndrome.

"PC-PLC" is phosphatidylcholine-specific phospholipase C. PC-PLC is thought to be involved in a signal transduction pathway that leads, via the transcription factor NF-κB to the activation of iNOS.

A "scavenger of NO" is a compound that by reacting with NO eliminates the ability of NO to act as a free radical. Similarly, a "scavenger of peroxynitrite" is a compound that by reacting with peroxynitrite eliminates the ability of peroxynitrite to act as a free radical.

ASPECTS OF THE INVENTION

In a general aspect, the present invention is a process of treating a disease of the central nervous system of a mammal (such as a human), the process comprising administering to the mammal a pharmacologically effective dose of one or more agents that are either 1) a nitric oxide scavenger, (2) a peroxynitrite scavenger, or (3) an agent that either interfere with the synthesis of iNOS in the cell or the enzymatic activity of iNOS in the cell.

An agent that inhibits the synthesis or enzymatic activity of iNOS is referred to here as an anti-iNOS agent.

A pharmacologically effective dose is one that slows or prevents the progression of the disease. It is preferable that the slowing or prevention not be accompanied by a toxic effect that offsets the medical value of slowing the progression of the targeted disease of the central nervous system.

In a particular embodiment of the treatment process, a pharmacologically active dose of a nitric oxide scavenger is administered, regardless of whether or not a peroxynitrite scavenger or an anti-iNOS agent is administered.

In another embodiment of the treatment process, a pharmacologically active dose of a peroxynitrite scavenger is administered, regardless of whether or not a nitric oxide scavenger or an anti-iNOS agent is administered.

In another embodiment of the treatment process, a pharmacologically active dose of an anti-iNOS agent is administered, regardless of whether or not a nitric oxide scavenger or a peroxynitrite scavenger is administered.

It is preferable to administer two or three independently acting agents than a single agent. Therefore one preferred embodiment of the process is the administration of both a nitric oxide scavenger and a peroxynitrite scavenger. Another preferred embodiment is the administration of both a nitric oxide scavenger and an anti-iNOS agent. Similarly, another preferred embodiment is the administration of both a peroxynitrite scavenger and an anti-iNOS agent. A fourth most preferred embodiment is the administration of a nitric oxide scavenger, a peroxynitrite scavenger, and an anti-iNOS agent.

The diseases of the central nervous system that are targets for this invention include those that, in addition to being a disease of the central nervous system, may affect or involve parts of the body other than the central nervous system. As a result, diseases that are targets for this invention include:
multiple sclerosis;
Alzheimer's disease;
AIDS with general symptoms;
amyotrophic lateral sclerosis;
cerebral malaria;
Pick's disease; and
any form of virus-induced encephalitis (e.g., herpes encephalitis).

Preferred nitric oxide scavengers are:
2-phenyl-4,4,5,5-tetramethylimidazoline-1-oxyl-3-oxide;
2- (4-carboxyphenyl) -4,4,5,5-tetramethylimidazoline-1-oxyl-3-oxide; and
2- (4-carboxymethoxyphenyl) -4,4,5,5-tetramethylimidazoline-1-oxyl-3-oxide.

The production of those nitric oxide scavengers is discussed in U.S. Pat. No. 5,464,857.

Preferred peroxynitrite scavengers are 2,6,8-trihydroxypurine (uric acid), dihydrorhodamine, and compounds that contain a thiol group (especially glutathione or cysteine). Uric acid is also considered to be an hydroxyl radical scavenger.

A preferred anti-iNOS agent is tricyclodecan-9-yl-xanthogenate.

Modes of Administration

Modes of administration of the various therapeutic agents used in the invention are exemplified in the Examples below. However, the agents can be delivered by any of a variety of routes including: by injection (e.g., subcutaneous, intramuscular, intravenous, intraarterial, intraperitoneal), by continuous intravenous infusion, orally (e.g., tablet, pill, liquid medicine), by implanted osmotic pumps (e.g., Alza Corp.), by suppository or aerosol spray.

Dosage

The extensive data in the Examples provide a useful starting point for calculating human dosage requirements.

For uric acid, the preferred dose range is normally between 1 mg/kg body weight/dose and 1 g/kg body weight/dose; one to three doses per day is normally preferred. However, if the uric acid is administered locally (e.g. at the site of inflammation) the dose may be as low as 10 μg/kg body weight.

For compounds that contain thiol groups (e.g., cysteine or glutathione) the preferred dose ranges and local site requirements are the same as those to those for uric acid.

Pharmaceutically Acceptable Salts

Pharmaceutically acceptable salts of the agents may be used, as may reagents such as appropriate esters that are modified by the body's enzymes to liberate the agent of interest.

EXAMPLES

Induction of EAE in rats by adoptive transfer of MBP-specific T cells or in SJL or SWXJ-14 mice by immunization with MBP or PLP 139-151, a peptide derived from MBP [8], results in variable disease. We have scored the clinical systems of EAE as tabulated below.

TABLE 1

Severity scores and symptoms of Experimental Allergic Encephalomyelitis

| Score | Clinical Symptoms |
|---|---|
| 1 | piloerection, tail weakness |
| 2 | tail paralysis |
| 3 | hind limb weakness/paralysis |
| 4 | hind and forelimb paralysis |
| 5 | moribund |

As we have previously described, the severity of clinical symptoms of EAE, as well as viral encephalopathies that are possibly immune-mediated, evidently correlates with NO production in the CNS [14]. We have determined that the site of major NO production varies between different EAE models. FIG. 1 shows the results of NO measurement in the brains and spinal cords of rats with adoptive transfer EAE versus SWXJ-14 mice with immunization-elicited EAE. The adoptive transfer of MBP-specific T cells in Lewis rats causes NO production which is largely limited to the spinal cord while immunization of SWXJ-14 mice with PLP 139-

151 results in the elaboration of high levels of NO in both spinal cord and brain.

In FIG. 1, EAE was elicited in 11 week old female Lewis rats by the adoptive transfer of 20×10⁶ cells of the MBP-specific line 5HGBP.G5 activated by stimulation with MBP and syngeneic APC 48 hours previously and NO levels measured 5 days after transfer. In SWXJ-14 mice, EAE was triggered by two subcutaneous immunizations (d.0 and 7) with 100 μg PLP in CFA over two injection sites, and NO levels measured 18 days later. Results expressed represent the mean values obtained from a minimum of 4 animals. Peak severity of the symptoms of EAE ranged from 2–3 for the rats and 4–5 for the mice. NO was semi-quantitated using spin trapping with DETC and EPR-spectroscopy as described previously [2,10].

Our initial studies in rats with EAE elicited by the adoptive transfer of MBP-specific T cells and in SJL mice immunized with MBP showed that i.p. administration of PTIO or its water soluble derivative carboxy-PTIO (c-PTIO) could forestall the appearance of clinical symptoms of EAE as well as reduce levels of NO detected in spinal cord by spin-trapping and EPR spectroscopy (Table 2).

TABLE 2

Effects of PTIO and carboxy-PTIO treatment on adoptive transfer EAE in Lewis rats and on immunization-elicited EAE in SJL mice

| EAE model[1] | Treatment[2] | NO-spinal[3] cord (mM) | Clinical[4] severity |
|---|---|---|---|
| Rat-adoptive transfer | none | 12.3 | 3 |
|  | PTIO | undetectable | 0.8 |
| SJL mouse - immunization | none | 2.4 | 1.5 |
|  | PTIO | 1.6 | 0.8 |
|  | c-PTIO | 1.4 | 0.7 |

Figure 2:
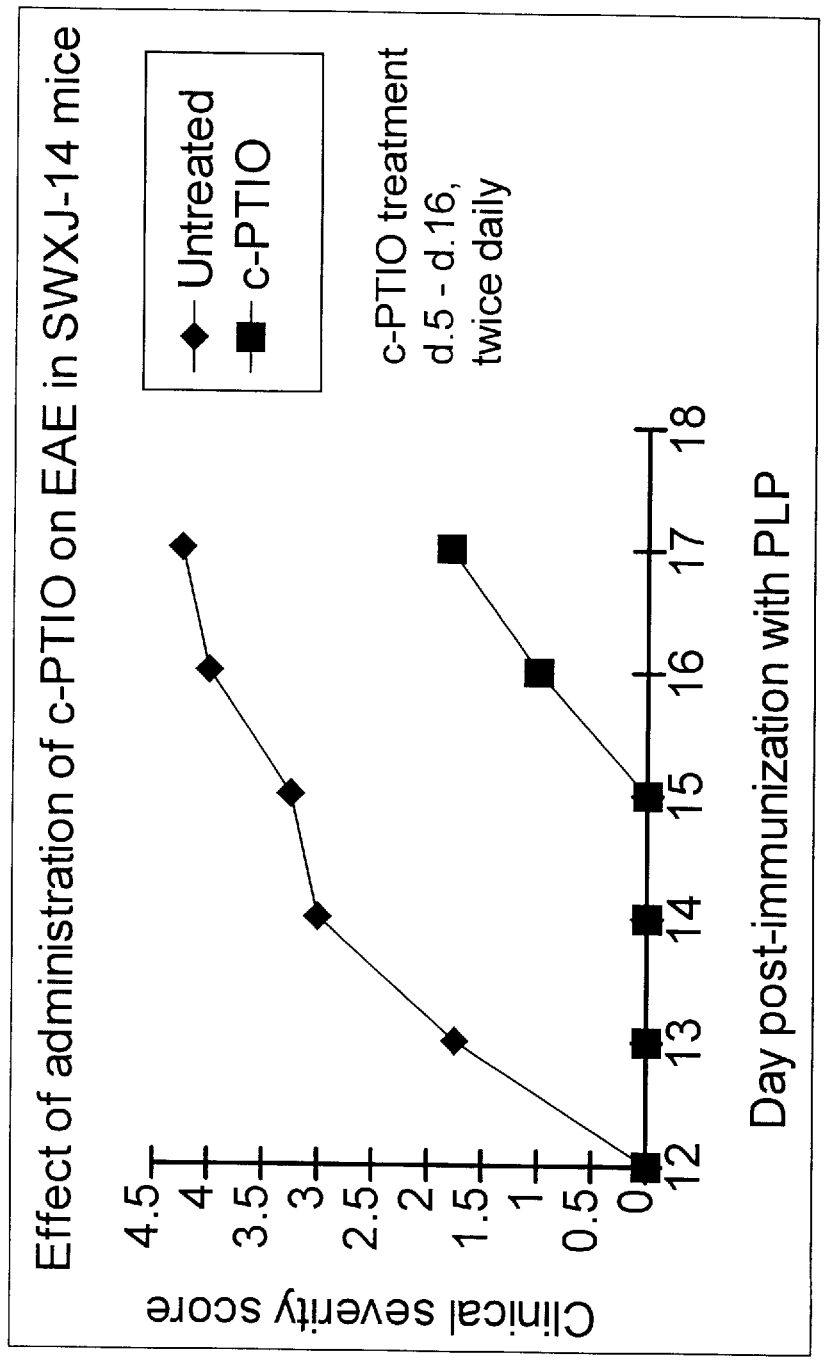
FIG. 2. Effect of daily administration of c-PTIO (carboxy-PTIO) on EAE in SWXJ-14 mice. EAE was induced in SWJX-14 mice by two subcutaneous immunizations (d.0 and d.7) of 100 mg PLP in CFA over two injection sites. Mice (N=3) were treated beginning on day 5 post-immunization with 2 mg/mouse c-PTIO twice daily i.p. and was continued until day 16 post-immunization (day 0 being the day of first immunization). Mean severity scores were graded as detailed in Table 1.
Figure 3:
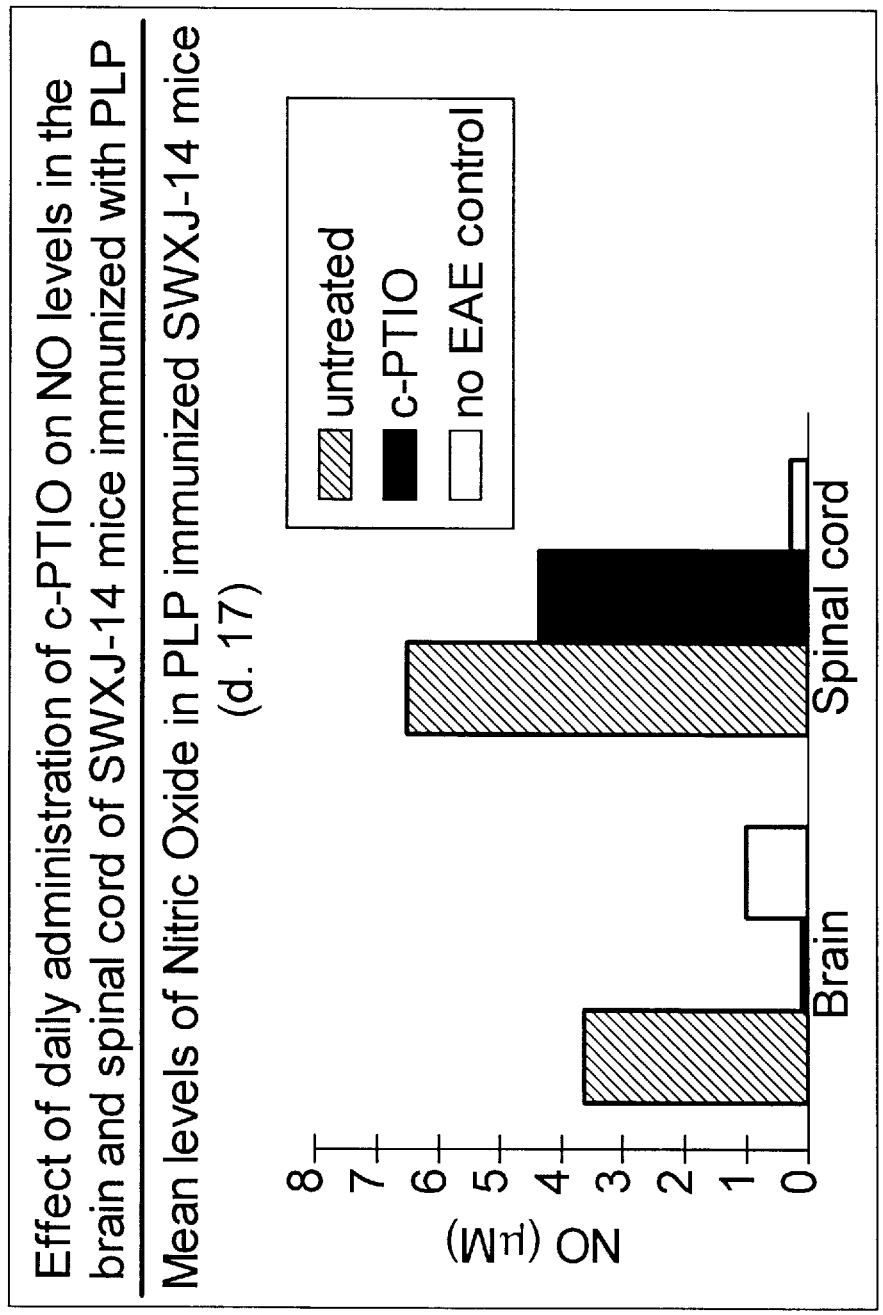
FIG. 3. Effect of daily administration of c-PTIO on NO levels in the brain and spinal cord of SWXJ-14 mice immunized with PLP. SWXJ-14 mice were immunized as described below for FIG. 1. Beginning 4 days post immunization, mice (n=7) were treated with 2 mg c-PTIO given i.p. until 16 days post-immunization. Mean severity scores were graded as detailed in Table 1. Mean nitric oxide levels in brain and spinal cord were semi-quantitated using spin-trapping with DETC and EPR spectroscopy at 17 days post-immunization as described elsewhere [2,10]. (For brain or spinal cord results are represented as follows: Left hand column: untreated. Center column: treated with c-PTIO. Right hand column: no EAE control)

In contrast to Lewis rats and SJL mice which often exhibit only mild symptoms and recover from EAE, SWXJ-14 mice immunized against myelin undergo a progressive, often fatal form of EAE. Clinical symptoms manifest as an ascending paralysis approximately 13 days after immunization and the disease rapidly progresses to its fatal endpoint by day 16–20. As is apparent form the results represented in FIG. 2 daily treatment of SWXJ-14 mice with two doses of 100 mg/kg carboxy-PTIO, commencing 4 days following immunization with PLP, delays the onset and reduces the severity of the clinical symptoms of EAE. NO levels in the brains and spinal cords of animals treated with a single daily dose of PTIO were semi-quantitated by spin trapping and EPR spectroscopy on day 17 after immunization, one day after treatment was terminated. Interestingly, the mice treated with carboxy-PTIO had low levels of NO in brain tissue compared to untreated PLP-immunized controls while spinal cord NO had already reached significant levels (FIG. 3). These were, however, somewhat less than the spinal cord NO levels detected in the surviving untreated animals. We expect that the removal of NO by PTIO should not necessarily interfere with the induction of the response responsible for NO production and that as the supplied PTIO is used up NO levels should rapidly return to control values.

Figure 5:
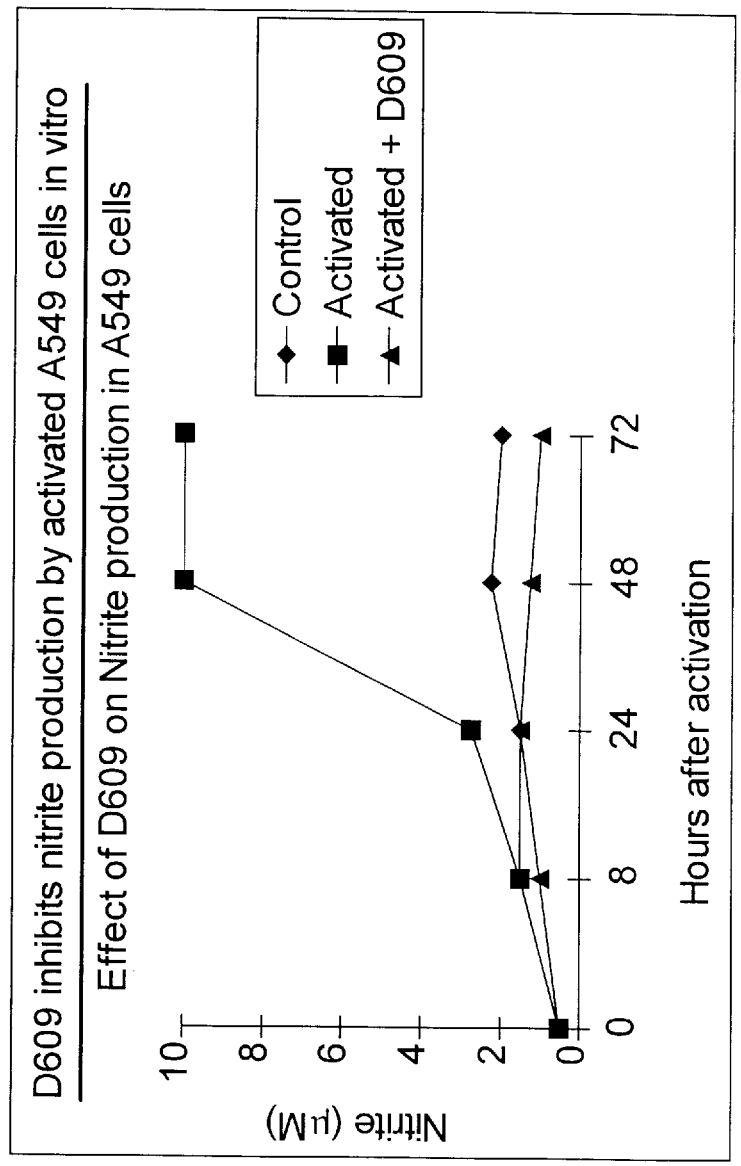
FIG. 5. D609 inhibits nitrite production by activated A549 cells in vitro. The accumulation of nitrite over time was measured in the presence and absence of D609. Human A549 cells were activated with IL-1β (100 units/ml), γIFN (500 units/ml) and TNFα (10 ng/ml), and the accumulation of nitrite over time was measured using the Griess reaction [15]. The concentration of nitrite was calculated using a standard solution of nitrite in culture media.

We have employed the human lung carcinoma cell line A549 (ATCC) and, as for comparison, the mouse monocyte-macrophage cell line RAW 264.7 (ATCC) as producers of NO. Treatment of RAW 264.7 cells with 1 μg/ml of LPS or A549 cells with IL-1β (100 units/ml), γIFN (500 units/ml), and TNFα (10 ng/ml) stimulates the production of NO which can be detected by the accumulation of nitrite in culture supernatants. Using these methods of stimulation, RAW cells produced up to 100 μM of nitrite during 24 hours of culture while the A549 cells generally produced roughly 10 fold less nitrite in our experiments. As shown in FIG. 5 inclusion of D609 (50 μg/ml) in the culture medium completely inhibited nitrite production by the A549 cells. Three other PLC inhibitors also blocked nitrite accumulation in cultures of both mouse and human cells (data not shown).

Figure 6:
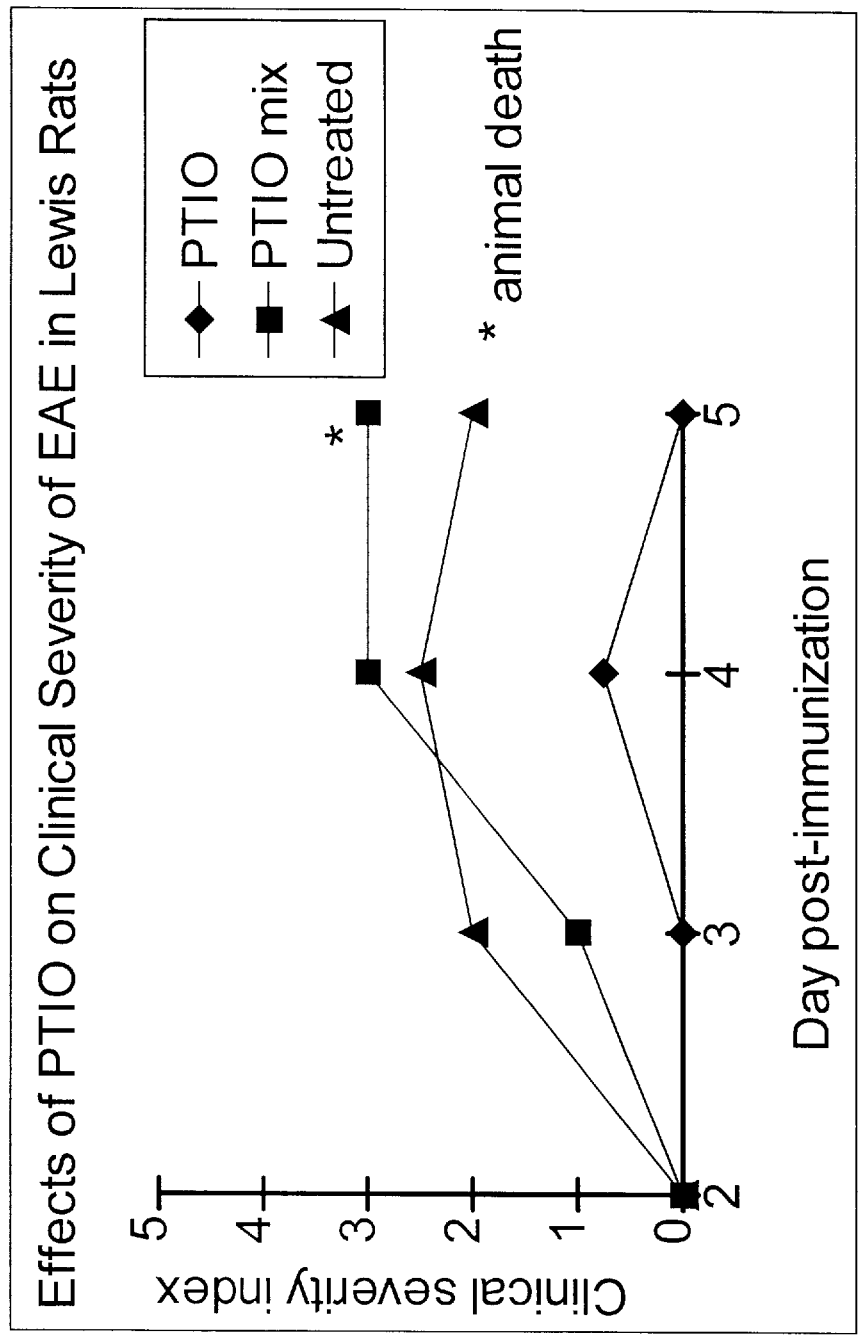
FIG. 6. Effects of PTIO on clinical severity of EAE in Lewis rats.

Rats were injected i.v. with 20×10⁶ MBP-specific CD4 T cells activated in vitro. Two days later the animals were treated with a single dose of either PTIO (20 mg) or a mixture of PTIO (20 mg), indomethacin (1 mg), and allopurinol ( 13 mg). Treatment was continued on a daily basis until day 4 and animals were sacrificed for NO measurement the following day. As shown in FIG. 6 rats treated with PTIO alone exhibited little or no symptoms of disease, while treatment with the mix had little effect.

Figure 7:
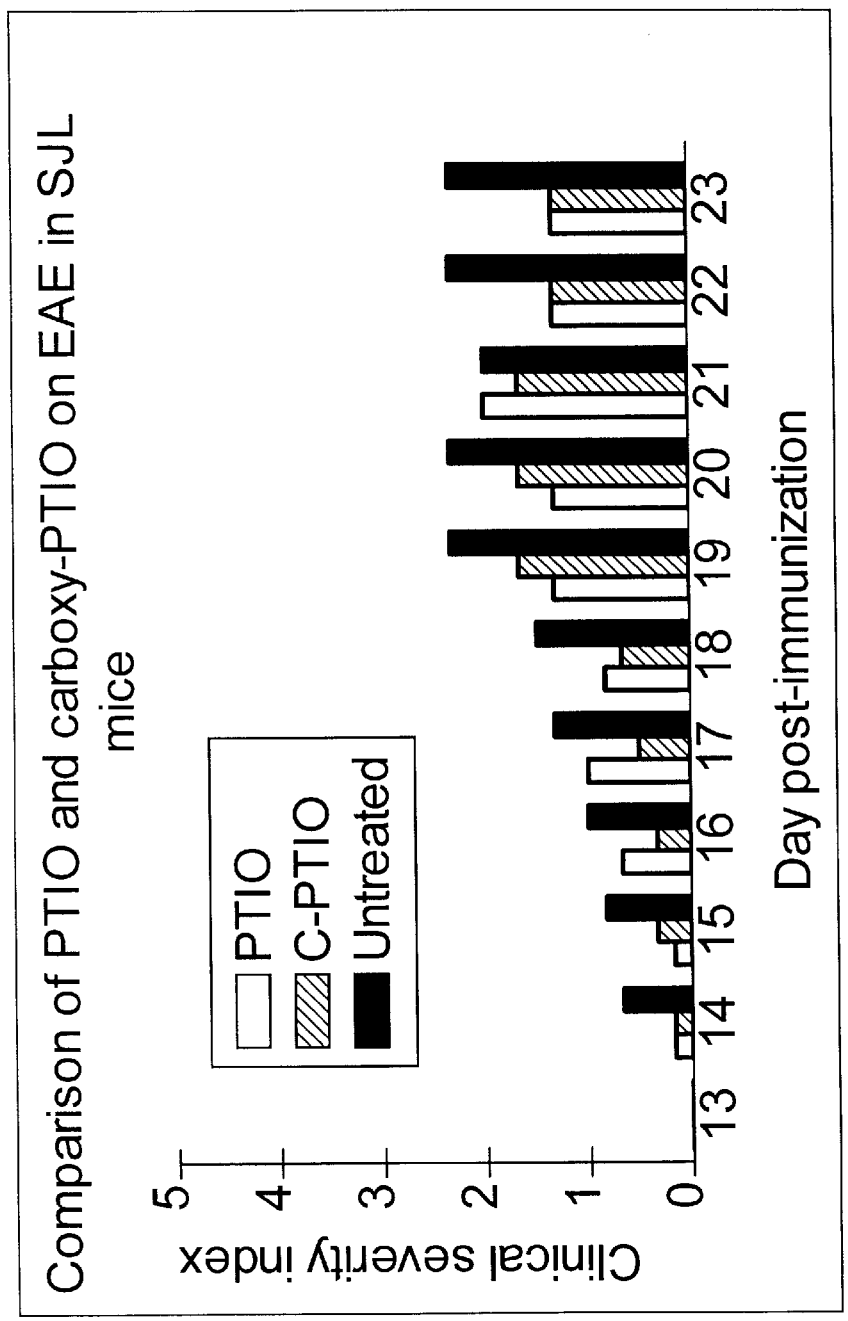
FIG. 7. Comparison of PTIO and carboxy-PTIO on EAE in SJL mice. For each day, the left hand column represent results for PTIO-treated mice, the center column shows results for c-PTIO-treated mice, and the right hand column shows results for untreated mice.
Figure 8:
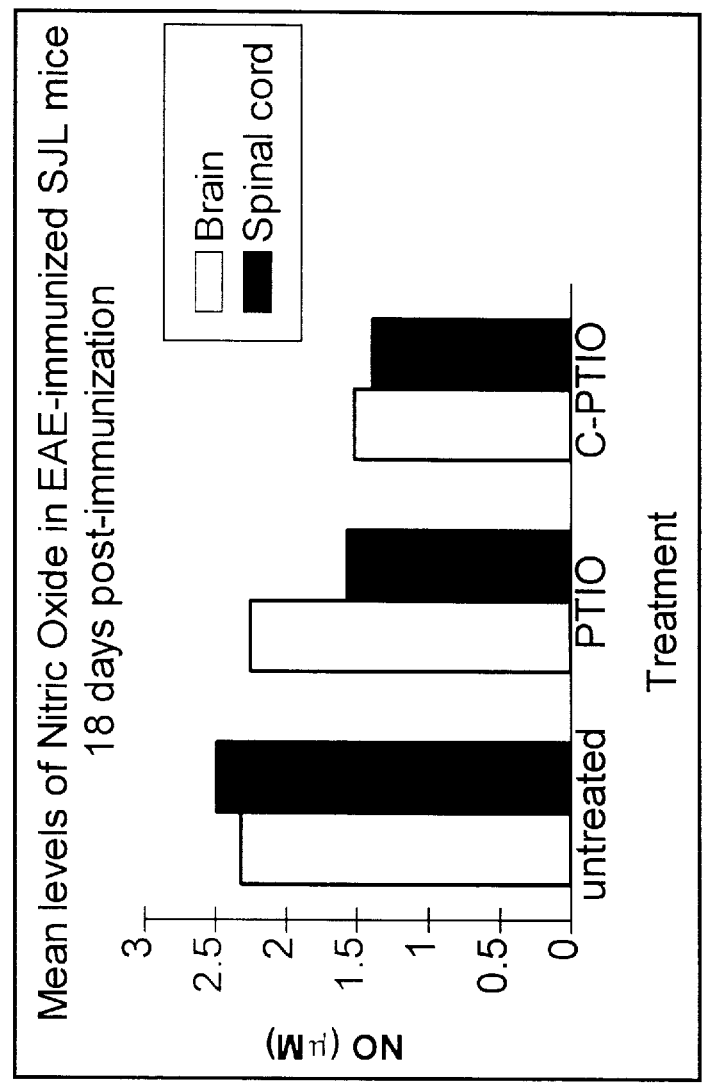
FIG. 8. Mean levels of Nitric Oxide in EAE immunized SJL mice 18 days post-immunization.

Since the PTIO is not water soluble (it can be administered in a lipid formulation) and therefore somewhat problematic in use, especially at the doses employed, we next compared the effectiveness of PTIO and a water soluble derivative, carboxy-PTIO [2-(4-Carboxyphenyl)-4,4,5,5-tetramethylimidazoline-1-oxyl-3-oxide] in other models of EAE to establish whether or not these compounds have a similar therapeutic effect. FIG. 7 shows the results of this comparison. SJL mice are immunized subcutaneously with pMBP in adjuvant to induce EAE, from which they often recover. Commencing ten days post-immunization, groups of mice (n=6) were treated once daily with 2 mg of either PTIO or carboxy-PTIO intraperitoneally and observed for clinical signs of EAE which were graded as detailed in Table 1. Both PTIO and carboxy-PTIO treated mice exhibited delayed onset of disease and somewhat lessened severity by comparison with untreated animals. At 18 days post-infection, NO determinations were performed in several mice from each group. The NO levels detected were lower in the spinal cords of mice treated groups with PTIO and carboxy-PTIO (FIG. 8). The minimal increase in brain NO caused by the induction of EAE was also inhibited by carboxy-PTIO (FIG. 8).

Figure 9:
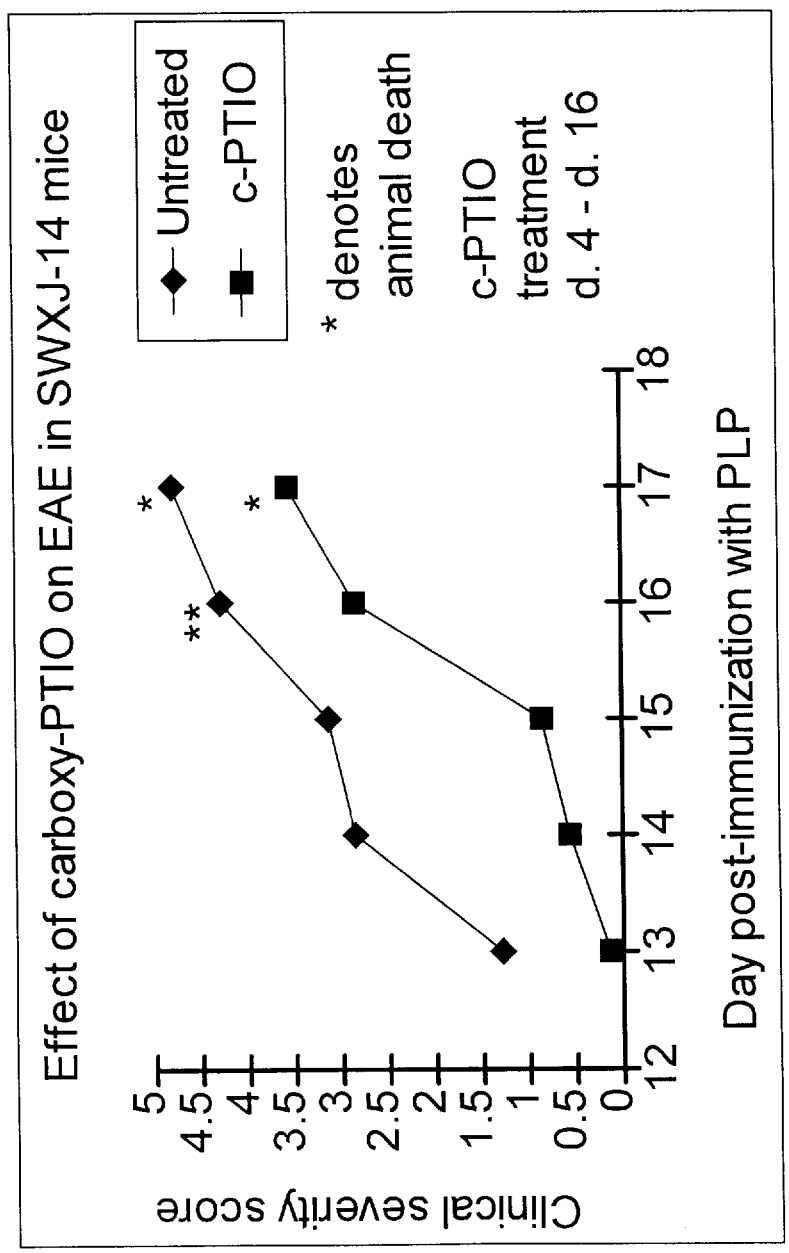
FIG. 9. Effect of Carboxy-PTIO on EAE in SWXJ-14 mice.
Figure 10:
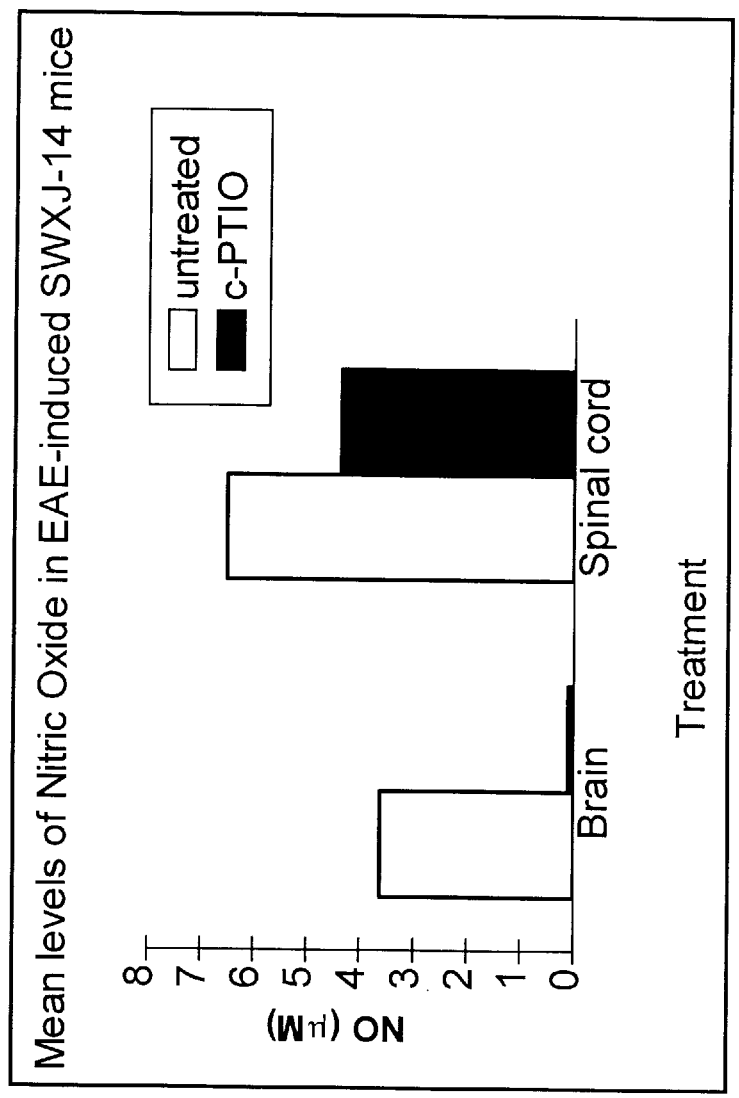
FIG. 10. Mean levels of Nitric Oxide in EAE-reduced SWXJ-14 mice. (For the results with the brain, and the results for the spinal cord, the left hand column represent results with untreated mice, the right hand column represents results with c-PTIO-treated mice.)
Figure 11:
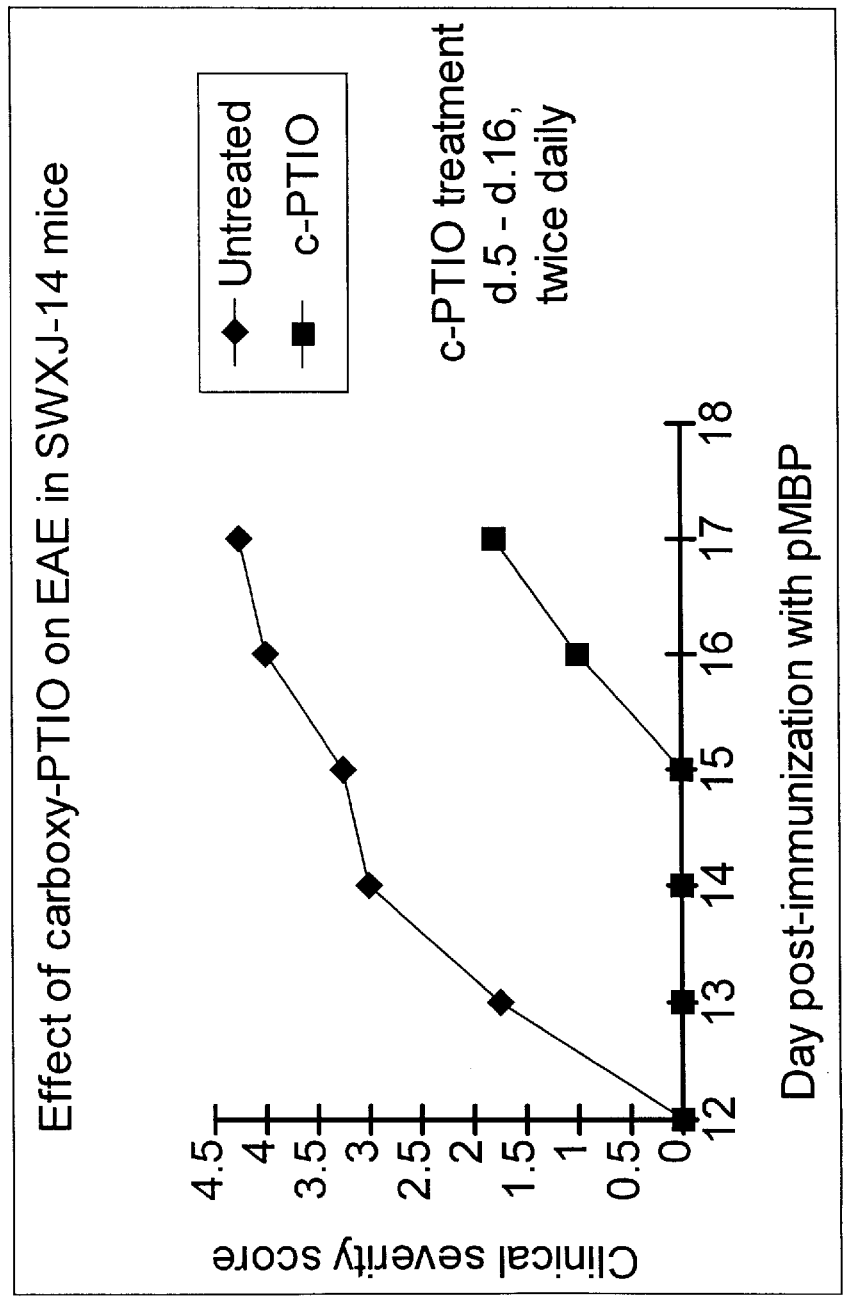
FIG. 11. Effect of carboxy-PTIO on EAE in SWXJ-14 mice.

In contrast to SJL mice, SWX mice immunized with PLP undergo a progressive, often fatal form of EAE. Clinical symptoms manifest as an ascending paralysis approximately 13 days after immunization and the disease rapidly progresses to its fatal endpoint by days 16–20. As is apparent from the results represented in FIG. 9, treatment of SWX mice with a single daily dose of 100 mg/kg mg carboxy-PTIO, commencing 4 days following immunization with PLP, delays the onset and reduces the severity of the clinical symptoms of EAE. Interestingly, when NO levels were semi-quantitated on day 17 after immunization, carboxy-PTIO treatment had evidently prevented the induction of NO in brain while spinal cord NO had already, one day after treatment had concluded, reached significant levels (FIG. 10). These did however remain somewhat less than the spinal cord NO levels detected in the surviving untreated animals. FIG. 11 shows that treatment of PLP-immunized SWXJ-14 mice with two daily doses of approximately 2 mg carboxy-PTIO dramatically improves the clinical course of EAE by comparison with a single daily dose (FIG. 9). We conclude that the amount of carboxy-PTIO we administered, especially considering the short in vivo half life of the compound, was only sufficient to delay the onset of the EAE in the SWXJ-14 mouse. Nevertheless, carboxy-PTIO administration limited NO production to the spinal cord and had a clear therapeutic effect in these animals despite their exaggerated EAE.

The fact that the onset of the clinical symptoms of EAE can be delayed and their severity diminished by treatment with NO scavengers confirms that NO is involved in the pathogenesis of this MS-related autoimmune process. Since EAE mediated by T cell transfer, which circumvents the activation of the antigen-specific elements of immunity involved in the disease process, can also be successfully treated with carboxy-PTIO, we conclude that NO is intimately involved in the end or effector stage of the disease. Thus, PTIO treatment should be effective regardless of the nature of the stimuli and cells involved in the production of NO. A significant feature of this aspect of the action of PTIO is that blocking the effects of NO by removing the molecule may not influence the immune mechanisms leading to its production and, more importantly, the regulatory processes that may eventually control the disease process. Thus, we would not expect that treatment with PTIO would interfere with whatever mechanism is involved in the periods of spontaneous remission often seen in patients with MS.

Figure 4:
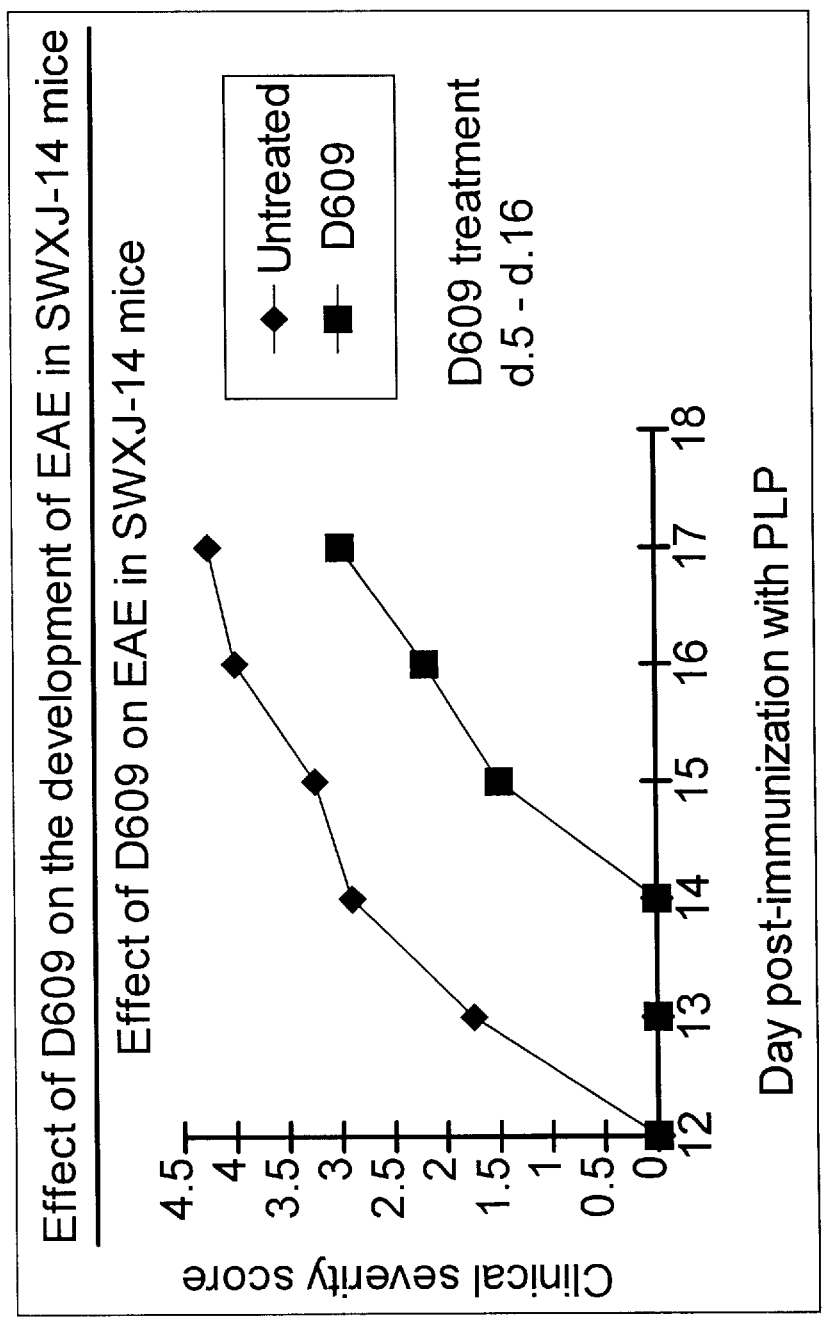
FIG. 4. Effect of D609 on the development of EAE in SWXJ-14 mice. SWXJ-mice were immunized with PLP as detailed for FIG. 2. Mice (n=2) were treated i.p. with 1 mg/mouse D609 from day 5 through day 14 post-immunization. Mean severity scores were graded as detailed in Table 1.

A second approach towards the inhibition of toxic NO-related effects in chronic neurological diseases is to interfere with the induction of the enzyme responsible for the formation for NO, iNOS. To this end we have employed the xanthogenate D-609 which inhibits the induction of iNOS by blocking the activation of phosphatidylcholine-specific phospholipase C (PC-PLC). PC-PLC activation is a proximal step in the signal transduction pathway that leads to the activation of iNOS [16]. As can be seen from the results expressed in FIG. 4, daily administration of 1 mg D-609 delays the onset of the clinical symptoms of EAE.

The biological half-life of carboxy-PTIO are estimated to be less than five minutes in the blood when injected i.v. or i.p. into either rats or mice. Approximately 75% of the PTIO administered to mice can be accounted for in excretions within 4 hours [17]. Nevertheless, the clinical symptoms of animals subjected to the stimuli that induce EAE and treated with PTIO are clearly alleviated for at least 24 hours between doses. This suggests that although the action of PTIO in vivo may be very short-lived, the effects of its activity are longer lasting. It is possible that the removal of a significant quantity of NO may reduce the amount of tissue damage to a level that the animal can cope with. However, we believe that it is possible that the transient reduction of NO accumulation in an inflammatory response may have more wide ranging effects for instance through the disturbance of regulatory circuits effecting the production of NO or one of the other related substances involved in immuno-pathology. Another possibility, suggested by the difference between spinal cord and brain in the "recovery" of NO levels in EAE following withdrawal of PTIO treatment, is that PTIO treatment may have a protective effect by maintaining the integrity of the blood brain barrier. Through its effects on the circulation, NO may play a role in facilitating access of MBP specific T cells to the brain which could be inhibited by PTIO. It is also conceivable that a PTIO derivative formed by its interaction with NO also has some protective effect. Whatever the case, we conclude that the NO scavenger PTIO has a strong therapeutic effect in EAE without notable side-effects which may be considered possible due to the normal actions of NO in other physiological systems. The fact that the onset of the clinical symptoms of EAE can be delayed and their severity diminished by reducing brain and spinal cord NO levels through treatment with NO scavengers, tends to substantiate the hypothesis that NO may be involved in the pathogenesis of this autoimmune process. Also noteworthy is the finding that PTIO treatment is effective when commenced after the disease process has been initiated. PTIO treatment is effective when started 4–5 days after immunization with myelin antigens and EAE mediated by T cell transfer, which circumvents the activation of the antigen-specific elements of immunity involved in the disease process, can also be successfully treated with carboxy-PTIO. In addition, the rapid onset of symptoms of EAE, and spinal cord production, when PTIO treatment is withdrawn also argues that both inflammatory myelin-specific T cells and macrophages are present and may be active in the spinal cords of the treated animals. We therefore conclude that the action of PTIO, and therefore No, is intimately involved in the end or effector stage of the disease. Thus, PTIO treatment should be effective regardless of the nature of the stimuli and cells involved in the production of NO. A significant feature of this aspect of the action of PTIO is that blocking the effects of NO by removing the molecule may not influence the immune mechanisms leading to its production and, more importantly, the regulatory processes that may eventually control the disease process. Thus, we would expect that treatment with PTIO would not interfere with whatever mechanism is involved in the periods of spontaneous remission often seen in patients with MS.

Figure 12:
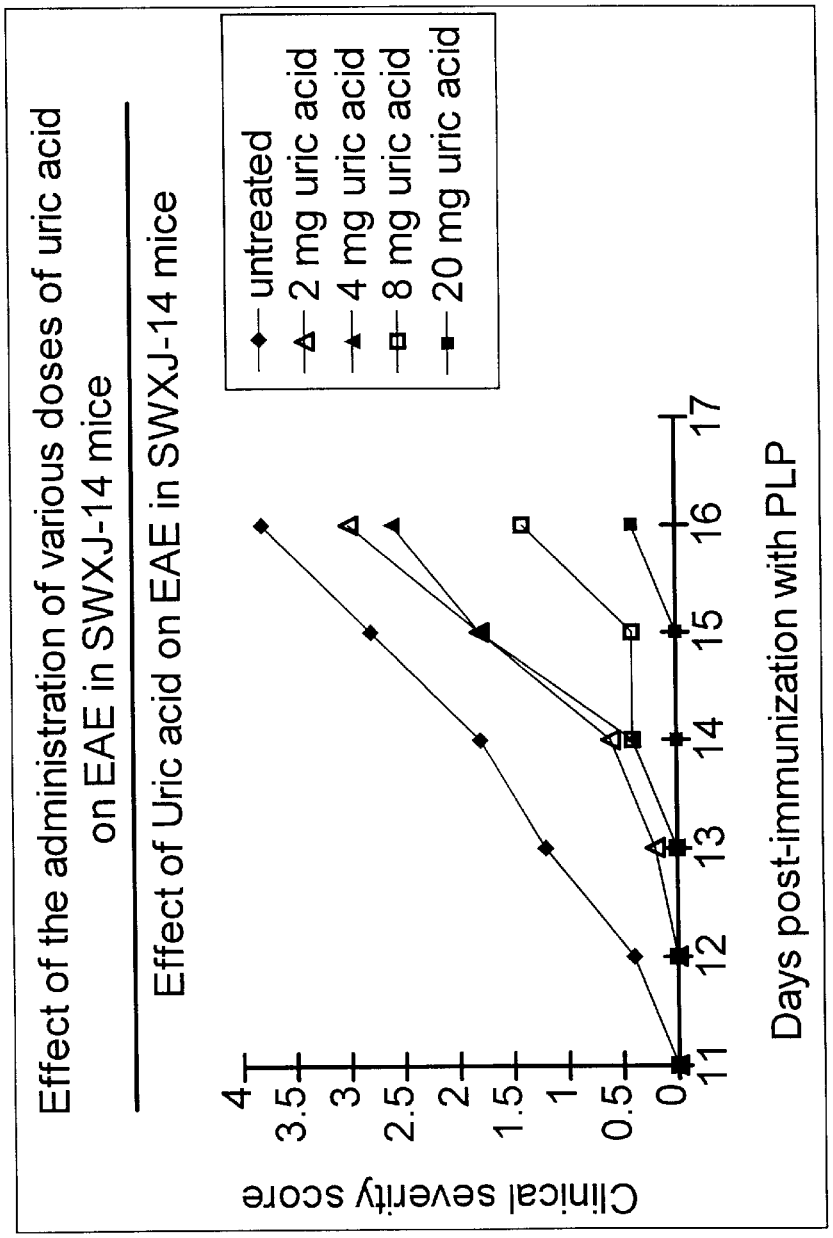
FIG. 12. Effect of the administration of various doses of uric acid on EAE in SWXJ-14 mice. EAE was induced in SWXJ-14 mice by two subcutaneous immunizations (d.0 and 7) of 1900 mg PLP in CFA over two injection sites. Mice (n=5) were treated once daily, beginning on day 5 post-immunization, with the indicated doses of uric acid. Mean severity scores were graded as detailed in Table 1.

NO is not universally considered to be a molecule with significant in vivo toxicity and peroxynitrite is thought to be the more toxic molecule produced by activated inflammatory cells resulting from the interaction of NO and superoxide. We would henceforth expect that removal of NO would reduce peroxynitrite formation. To determine whether NO or peroxynitrite is more likely to be ultimately responsible for clinical disease in EAE we have performed a series of experiments using uric acid, a known scavenger of peroxynitrite, to treat EAE induced in SWXJ-14 mice by immunization with PLP. As demonstrated in FIG. 12, uric acid treatment commencing at day 5 postimmunization delays the onset and severity of the clinical symptoms of EAE in these animals in a dose dependent fashion. The majority of the mice treated with a high dose of uric acid remained healthy throughout the length of the experiment.

At 16 days after immunization, several mice from each group were euthanized so that NO levels in their brains and spinal cords could be measured using spin-trapping and EPR spectroscopy.

Figure 13:
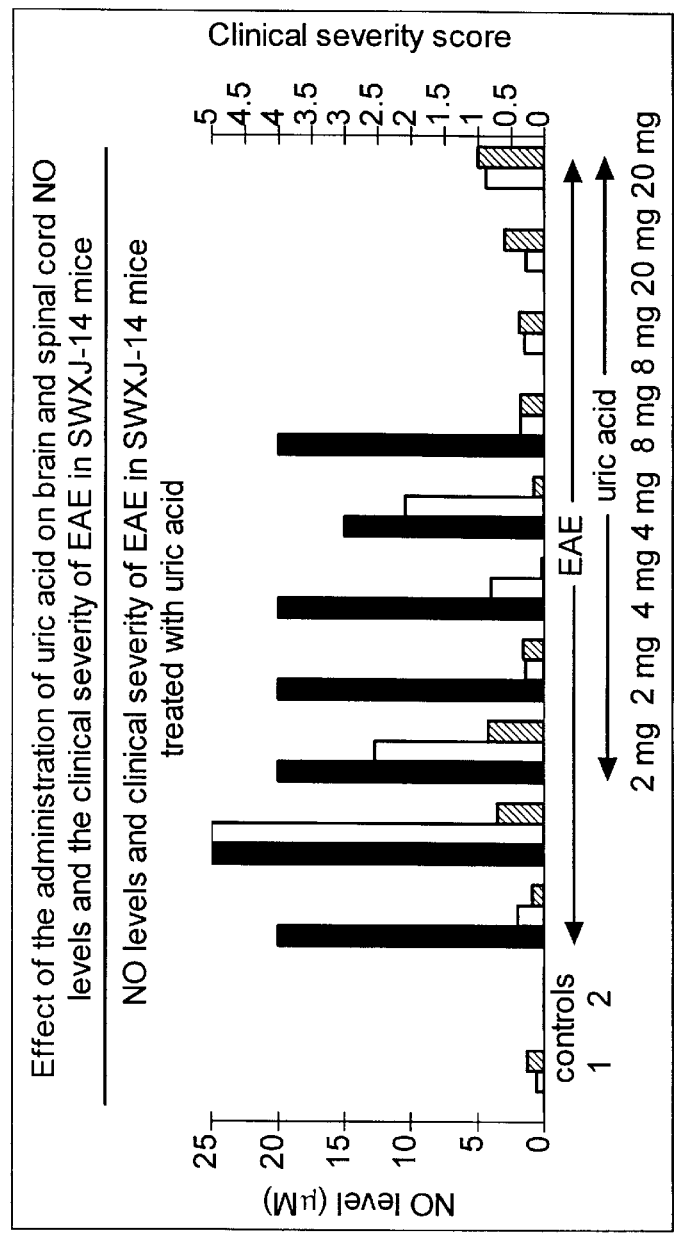
FIG. 13. Effect of the administration of uric acid on brain and spinal cord NO levels and the clinical severity of EAE in SWXJ-14 mice. SWXJ-14 mice were immunized with PLP in CFA as described for FIG. 12 and treated once daily with the indicated doses of uric acid i.p. At day 16 post-immunization the animals were euthanized and NO levels in brain and spinal cord assessed as detailed for FIG. 3. Results are for individual mice. Each central white column represents the spinal cord NO level. The black column to the left of a white column represents the clinical severity score. The cross hatched column to the right of a white column represents the brain NO level.

As can be seen in FIG. 13, significant levels of NO were detected in spinal cord and brain of mice treated with uric acid that failed to show symptoms of EAE. We therefore conclude that NO itself may not be entirely responsible, directly, for clinical disease in EAE and that peroxynitrite has a major role.

Figure 14:
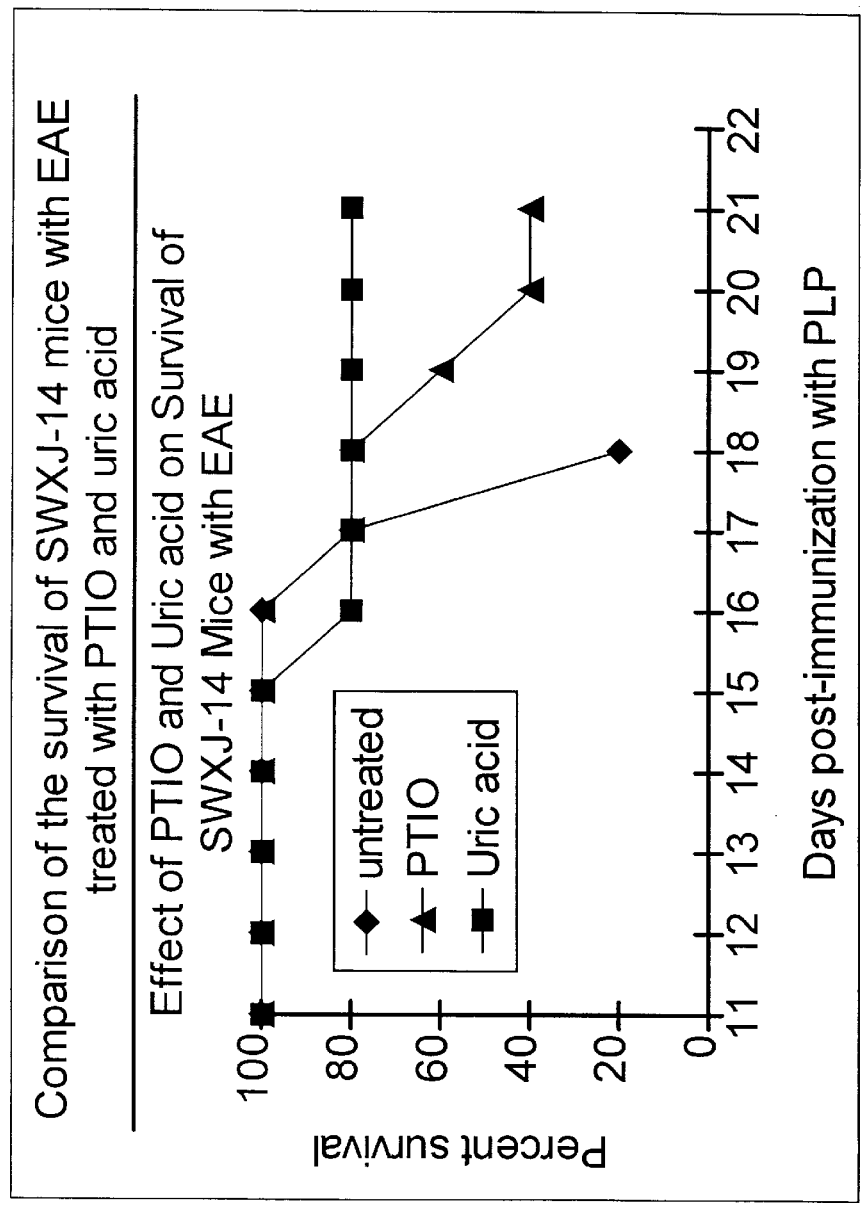
FIG. 14. Comparison of the survival of SWXJ-14 mice with EAE treated with PTIO and uric acid. SWXJ-mice were immunized with PLP in CFA as described for FIG. 12 and treated once daily with a 2 mg dose of uric acid or PTIO i.p. from day 5 to day 13, followed by two daily doses on day 14 and three daily doses thereafterward.

To more directly compare the action of PTIO and uric acid in EAE we have administered each of these agents in parallel to PLP-immunized SWXJ-14 mice. In these experiments the mice were immunized with PLP and treated with increasing doses of PTIO or uric acid beginning at day 5 after immunization. FIG. 14 shows the results of a representative experiment.

While the untreated controls died or were euthanized due to severe disease by day 18, 40 and 80% of the mice treated with PTIO and uric acid, respectively, were still alive several days later and a number were actually beginning to show some improvement in the clinical signs of their disease when the experiment was terminated. This suggests the possibility that treatment with scavengers of NO and, particularly, peroxynitrite may allow SWXJ-14 mice suffering from EAE to undergo remission, which is an exceedingly rare event in this model. A distinct but allied approach towards the inibition of toxic NO-related effects in chronic neurological diseases is to interfere with the induction of the enzyme responsible for the formation of NO,iNOS. Towards this end we have employed the xanthogenate D-609 which inhibits the induction of iNOS by blocking the activation of phosphatidylcholine-specific phospholipase C (PC-PLC). PC-PLC activation is a promixal step in the signal transduction pathway that leads to the activation of iNOS [16]. As can be seen from the results expressed in FIG. 4, daily administration of 1 mg D-609 delays the onset of the clinical symptoms of EAE elicited by pMBP immunization of SWXJ-14 mice.

Separate experiments involving gel-shift assays, not described in detail here, showed that D609 (50 µg/ml) inhibits the transcriptional activation of the iNOS gene in human A549 cells activated with 1 µg/ml of LPS (bacterial lipopolysaccharide) and mouse RAW 264.7 cells activated with a mixture of IL-1β (100 units/ml), γIFN (500 units/ml) and TNFα (10 ng/ml), also that the activation of the transcription factor NF-κB in those human and mouse cells.

References

1. Schmidt, H. H. H. W. and U. Walter (1994). "NO at work." *Cell* 78:919–925.
2. Hooper, D. C., T. S. Ohnishi, et al. (1995). "Local nitric oxide production in viral and autoimmune diseases of the central nervous system." *P.N.A.S.* 92: 5312–5316.
3. Synder, S. H. and D. S. Bredt (1992). "Biological roles of nitric oxide." *Sci.Amer. May:* 68–77.
4. Akgoren, N., M. Fabricius, et al. (1994). "Importance of nitric oxide for local increases of blood flow in rat cerebellar cortex during electrical stimulation." *P.N.A.S.* 91: 5903–5907.
5. Beckman, J. (1994). "Peroxynitrite versus hydroxyl radical: The role of nitric oxide in superoxide-dependent cerebral injury." *Annals of the New York Academy of Sciences* 738: 69–72.
6. Bagasra, O., Michaels, F. H., Zheng, Y. M., Bobroski, L. E., Spitsin, S. V., Fu, Z. F., Tawadros, R., and Koprowski, H. (1995). "Activation of the inducible form of nitric oxide synthase in the brains of patients with multiple sclerosis". *P.N.A.S.* 92 12041–12045.
7. Ben-Nun, A., H. Wekerle, et al. (1981). "The rapid isolation of clonable antigen-specific T lymphocyte lines capable of mediating autoimmune encephalomyelitis". *Eur.J.Immunol.* 11: 195–199.
8. Knobler, R. L., Lublin, F. D., Linthicum, D. S., Cohn, M., Melvold, R. D., Lipton, H. L., Taylor, B. A. and Beamer, W. G. (1988). "Genetic regulation of susceptibility and seventy of demyelination". *Ann.NY.Acad..Sci.* 540, 735–737.
9. Korngold, R., Feldman, A., Rorke, L. B., Lublin, F. D., and Doherty, P. C. (1986). "Acute experimental allergic encephalomyelitis in radiation bone marrow chimeras between high and low susceptible strains of mice". *Immunogenetics* 24, 309–315.
10. Lin, R. F., T.-S. Lin, et al. (1993). "Nitric oxide localized to spinal cords of mice with experimental allergic encephalomyelitis: An electron paramagnetic resonance study." *J.Exp.Med.* 178: 643–648.

10. Cross, A. H., T. P. Misko, et al. (1994). "Aminoguanidine, an inhibitor of inducible nitric oxide synthase, ameliorates experimental autoimmune encephalomyelitis in SJL mice." *J.Clin. Invest.* 93: 2684–2690.
11. Zielasek, J., Jung, S. et al. (1995). "Administration of nitric oxide synthase inhibitors in experimental autoimmune neuritis and experimental autoimmune encephalomyelitis". *J. Neuroimmunol.* 58 81–88.
12. Akaike, T., E. Weihe, et al. (1995). "Effect of neurotropic virus infection on neuronal and inducible nitric oxide synthase activity in rat brain." *J.Neurovir.* 1: in press.
13. Tschaikowsky, K., Meisner, M., et. al. (1994). "Induction of nitric oxide synthase activity in phagocytic cells inhibited by tricyclodecan-9-yl-xanthogenate (D609)". *Br.J.Pharmacol.* 113, 664–668.
14. Koprowski, H., Zhen, Y. M., Heber-Katz, E., Fraser, N., Rorke, L., Fu, Z. F., Hanlon, C., and Dietzschold, B. (1993) In vivo expression of inducible nitric oxide synthase in experimentally induced neurologic diseases. Proc. Natl. Acad.Sci., 90:3024–3027.
15. Green, L. C., Wagner, D. A., Glogowski, J., Skipper, P. L., Wishnok, J. S., and Tannenbaum, S. R. (1982) Analysis of Nitrate, Nitrite and [$^{15}$N] Nitrate in Biological Fluids. Analytical Biochem., 126:131–138.
16. Tschaikowsky, K., Meisner, M., Schonhuber, F., and Rugheimer, E. (1994) Induction of nitric oxide synthase activity in phagocytic calls inhibited by tricyclodecan-9-yl-xanthogenate (D609). Br.J.Pharmacol., 113:664–668.
17. Akaike, T., Yoshida, M., Miyamoto, Y., Sato, K., Kohno, M., Sasamoto, K. Miyazadi K., Ueda, S., and Maeka, H. (1993) Antagonistic action of imidazolineoxyl N-oxides against endothelium-derived relaxing factor/NO through a radical reaction. Biochemistry, 32:827–832.

What is claimed is:

1. A process of treating a disease of the central nervous system of a mammal, which process comprises administering to the mammal a pharmacologically effective dose of uric acid wherein the disease of the central nervous system is selected from the group consisting of multiple sclerosis, Alzheimer's disease, AIDS with general symptoms, amyotrophic lateral sclerosis, cerebral malaria, Pick's disease, and a virus-induced encephalitis.

2. A process of claim 1 where the mammal is a human.

3. A process of treating a disease of the central nervous system of a mammal, wherein said disease involves the action of peroxnitrite, said process comprising the administration to the mammal of a pharmacologically effective dose of uric acid.

4. A process of claim 3 wherein the mammal is human.

5. A process of claim 2 wherein the disease is multiple sclerosis.

* * * * *

UNITED STATES PATENT AND TRADEMARK OFFICE
CERTIFICATE OF CORRECTION

PATENT NO : 5,872,124
DATED : February 16, 1999
INVENTOR(S): Koprowski et al.

It is certified that error appears in the above-identified patent and that said Letters Patent is hereby corrected as shown below:

Column 5, line 35, immediately under the horizontal line of Table 2, please insert the following:

--[1]EAE was induced in Lewis rats by adoptive transfer of MBP-specific T cells and in SJL mice by immunization as detailed in the legend to Figure 1. [2]Beginning on day 2, rats were treated daily with 100 mg/kg PTIO given i.p. Commencing ten days post-immunization, groups of mice (n=6) were treated once daily with 2 mg of either PTIO or carboxy-PTIO given i.p. [3]Spinal cord NO levels were determined by spin-trapping and EPR spectroscopy as previously described [2,10]. Measurements were taken on day 5 post-immunization for rats and day 18 post- immunization for mice. [4]Mean severity scores were graded at the time of sacrifice as detailed in Table 1.--

Signed and Sealed this

Second Day of May, 2000

Attest:

Q. TODD DICKINSON

*Attesting Officer*　　　　　*Director of Patents and Trademarks*